(12) United States Patent
Maltezos et al.

(10) Patent No.: US 8,975,065 B2
(45) Date of Patent: Mar. 10, 2015

(54) MEANDERING CHANNEL FLUID DEVICE AND METHOD

(75) Inventors: George Maltezos, Fort Salonga, NY (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 1861 days.

(21) Appl. No.: 11/880,836

(22) Filed: Jul. 23, 2007

(65) Prior Publication Data

US 2008/0044887 A1    Feb. 21, 2008

Related U.S. Application Data

(60) Provisional application No. 60/832,785, filed on Jul. 24, 2006.

(51) Int. Cl.
| | |
|---|---|
| *C12N 1/12* | (2006.01) |
| *C12M 1/00* | (2006.01) |
| *C12N 13/00* | (2006.01) |
| *C02F 3/32* | (2006.01) |
| *C10L 1/02* | (2006.01) |
| *C12M 1/12* | (2006.01) |
| *C12M 3/06* | (2006.01) |
| *C12P 3/00* | (2006.01) |
| *C12P 7/64* | (2006.01) |
| *B01J 19/00* | (2006.01) |

(Continued)

(52) U.S. Cl.
CPC .............. *C12N 13/00* (2013.01); *B01J 19/0093* (2013.01); *C02F 1/30* (2013.01); *C02F 3/327* (2013.01); *C02F 3/348* (2013.01); *C10L 1/026* (2013.01); *C12M 21/02* (2013.01); *C12M 23/06* (2013.01); *C12M 23/16* (2013.01); *C12M 31/04* (2013.01); *C12N 1/12* (2013.01); *C12P 3/00* (2013.01); *C12P 7/6463* (2013.01); *C12P 7/649* (2013.01); *Y02E 50/13* (2013.01)
USPC .................. 435/257.1; 435/292.1; 435/173.1; 435/173.9; 435/289.1; 435/283.1

(58) Field of Classification Search
None
See application file for complete search history.

(56) References Cited

U.S. PATENT DOCUMENTS

| | | |
|---|---|---|
| 2006/0288708 A1 | 12/2006 | Maltezos et al. |
| 2007/0012891 A1 | 1/2007 | Maltezos et al. |

(Continued)

FOREIGN PATENT DOCUMENTS

GB        2235210 A  *  2/1991

OTHER PUBLICATIONS

Hu, Q, Zhang, C. and Sommerfeld, M. "Biodiesel from Algae:Lessons Learned Over the Past 60 Years and Future Perspectives" Journal of Phycology, Apr. 2006, vol. 42 (s1), p. 12 (PSA Abstract No. 37).*

(Continued)

*Primary Examiner* — Jon P Weber
*Assistant Examiner* — Aaron J Kosar
(74) *Attorney, Agent, or Firm* — Steinfl & Bruno, LLP (57) ABSTRACT

Methods and devices of performing reactions for which presence of light is desirable are provided. Biological or chemical materials such as algae are put in a chamber shaped as a meandering fluid channel. The algae can be combined with biomass such as human or animal waste and then subject to light, such as natural light or light coming from a LED, to produce fuel. Production of fuel can be optimized by controlling the height-to-width ratio of the channels.

33 Claims, 8 Drawing Sheets

(51) Int. Cl.
*C02F 1/30* (2006.01)
*C02F 3/34* (2006.01)

(56) References Cited

U.S. PATENT DOCUMENTS

| | | |
|---|---|---|
| 2007/0045880 A1 | 3/2007 | Maltezos et al. |
| 2008/0013092 A1 | 1/2008 | Maltezos et al. |
| 2008/0069733 A1 | 3/2008 | Maltezos et al. |
| 2008/0083465 A1 | 4/2008 | Maltezos et al. |
| 2008/0133267 A1 | 6/2008 | Maltezos et al. |
| 2008/0142157 A1 | 6/2008 | Maltezos et al. |

OTHER PUBLICATIONS

Wu, H.; Odom, T.W.; Chiu, D.T.; and Whitesides, G.W., "Fabrication of Complex Three-Dimensional Microchannel Systems in PDMS", JACS, 2003, 125(2), pp. 554-559.*

Sheth, M; Ramkrishna, D; and Fredrickson, A.G. "Stochastic Models of Algal Photosynthesis in Turbulent Channel Flow" AIChE Journal, 1977, 23(6), pp. 794-804.*

Zhang, X. and Haswell, S.J. "Materials Matter in Microfluidic Devices", MRS Bull., Feb. 2006, 31, pp. 96-99.*

Wu, Jigang; Zheng Guoan; Lee, Lap Man "Optical Imaging Techniques in Microfluidics and Their Applications" Lab Chip, 2012 (published Jul. 4, 2012), 12, 3566-3575. DOI: 10.1039/c2lc40517b.*

Ashenhurst, J.A. "Polar Protic? Polar Aprotic? Nonpolar? All About Solvents" Master Organic Chemistry (URL: masterorganicchemistry.com/2012/04/27/polar-protic-polar-aprotic-nonpolar-all-about-solvents/), Apr. 27, 2012, accessed online Aug. 6, 2014), 22 pages.*

Kosourov S, Patrusheva E, Ghirardi ML, et al., "A comparison of hydrogen photoproduction by sulfur-deprived *Chlamydomonas reinhardtii* under different growth conditions", Journal of Biotechnology 128 (4): 776-787 (Mar. 10, 2007).

A. D. Stroock, S. K. Dertinger, A. Ajdari, I. Mezic, H.A. Stone, G. M. Whitesides "Chaotic Mixer for Microchannels", Science 25 vol. 295 No. 5555, pp. 647-651 (Jan. 2002).

T. You, S. M. Barnett "Effect of Light Quality on Production of Extracellular Polysaccharides and Growth Rate of *Porphyridium cruentum*", Biochem. Eng. J. vol. 19, No. 3, pp. 251-258. (2004).

C. Sorokin, R.W. Krauss "The Effects of Light Intensity on the Growth Rates of Green Algae", Plant Physiol. 33: 109-112 (1958).

* cited by examiner

MEANDERING CHANNEL FLUID DEVICE AND METHOD

CROSS REFERENCE TO RELATED APPLICATIONS

This application claims priority to U.S. Provisional Application Ser. No. 60/832,785 filed on Jul. 24, 2006, the disclosure of which is incorporated herein by reference it its entirety.

STATEMENT OF GOVERNMENT GRANT

The U.S. Government has certain rights in this invention pursuant to Grant No. HG002644 awarded by the National Institute of Health.

FIELD

The present disclosure relates to meandering fluid channel devices and methods.

BACKGROUND

Performance of reactions such as formation of biodiesel fuel starting from algae, waste and light is discussed, for example, in Hu Q, Zhang C, Sommerfeld M, Biodiesel from algae: Lessons learned over the past 60 years and future perspectives, Journal of Phycology 42: 12-12 37 Suppl. 1 Apr. 2006. See also Kosourov S, Patrusheva E, Ghirardi M L, et al., A comparison of hydrogen photoproduction by sulfur-deprived *Chlamydomonas reinhardtii* under different growth conditions, Journal of Biotechnology 128 (4): 776-787 Mar. 10, 2007.

SUMMARY

The present disclosure deals with methods and devices to perform reactions that are desirably performed in presence of light so that efficiency of the reaction is enhanced.

According to an aspect, the present disclosure deals with a different way to obtain optimum growth of algae given the space/light available. In particular, microfluidics can be used as a large surface area reaction chamber for chemical and biological reactions.

According to a first aspect, a method of reacting a biological or chemical material, is provided, the method comprising: providing a chamber shaped as a meandering fluid channel; placing the biological or chemical material in the chamber; subjecting the biological or chemical material to light for a time and under conditions to allow the biological or chemical material to react, wherein channels of the meandering fluid channel have a channel height and a channel width, and wherein the channel height to channel width ratio is chosen to optimize the reaction.

According to a second aspect, an energy source panel is provided, comprising: a chamber shaped as a meandering fluid channel; a plurality of channels, comprising a first series of channels adapted to contain gas and a second series of channels adapted to contain gas; one or more membranes separating the first series of channels from the second series of channels; and a light source, adapted to subject the algae to light.

According to a third aspect, a device is provided, the device comprising: a circuit comprising meandering fluid channels having a first index of refraction; the fluid channels comprising liquid having a second index of refraction, and algae; wherein a shape of an interface between the first index of refraction and the second index of refraction is so selected to maximize the amount of light incident on the circuit guided into the channels.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention. In the drawings.

DETAILED DESCRIPTION

The present disclosure, relates to a method of reacting a biological or chemical material. The term "material" as used herein refers to any substance comprising one or more chemical entities that can undergo a chemical transformation or change under appropriate conditions, which includes but is not limited to an interaction with chemical entities from a different material, and interactions among chemical entities in the same material. A "biological material" is a material that is biological in nature, a "chemical material" is a substance acting, operated or produced by chemicals, including but not limited to a substance obtained by a chemical process and/or producing a chemical effect.

In some embodiments, the chemical or biological material is reacted with a reactant, wherein the term "reactant" indicates a substance that enters into an/or is altered in the course of a chemical reaction, which includes but is not limited to a substance that interact with the biological and/or chemical material, and/or a substance that favors or promote a reaction involving the chemical or biological material.

In some embodiments, the reaction involving the chemical or biological material can result in a product, which includes but is not limited to any substance that is formed following the reaction of the chemical or biological material.

The following description will make reference to embodiments wherein the biological or chemical material is composed of algae, the reactant is biomass and the reaction results in the production of a fuel. Additional or alternative materials, reactants and/or products are identifiable by a skilled person upon reading of the present disclosure, will not be further described in detail.

In some embodiments, the present disclosure allows a more efficient production of biodiesel by providing a chamber (e.g., a microfluidic chamber) that is designed for optimum surface area, e.g. a microfluidic meandering channel.

Figure 1:
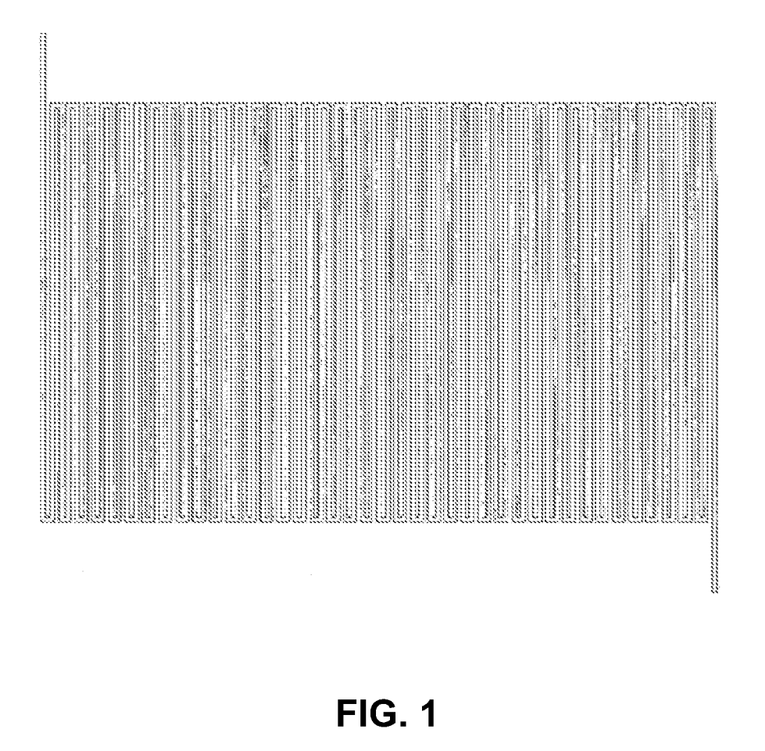
FIG. 1 shows a view from the top of a meandering channel.

A meandering channel is a channel with a plurality of meanders, twists or bends. The higher the number of meanders, the larger the meander ratio of the channel, i.e. the surface area of the channel. FIG. 1 shows a meandering channel comprising a plurality of channels (10), adapted for use with the present disclosure.

In accordance with an aspect of the present disclosure, solar panels or the like are obtained by 1) combining algae with human or animal waste or any biomass that the algae can feed off of in a, fluidic chamber optimized to maximize light/algae/feedstock reaction in order to maximize fuel production, and 2) subjecting the algae to light. In this way, the algae will 'eat' the waste and convert it to an oil ideally suited for biodiesel, i.e. fuel produced from the vegetable oils of the algae. Alternatively, some species of algae can form hydrogen instead of oil, as later discussed. A solvent can be used at the end to get the oily algae out.

Measures of optimization can be "efficiency" and "time efficiency". The goals are those of making use of all the waste and producing the most oil in the shortest time. Efficiency can be measured as volume of oil divided by volume of waste. In other words, efficiency measures volume or mass of oil produced per amount of waste. Time efficiency can be measured as volume of oil divided by unit time. Efficiency and time efficiency can each have different optimum points. Quicker or bigger bioreactors might not use all the waste available.

The solvent to be used to push the algae out and dissolve the oil can be hexane or a supercritical fluid.

The chamber or circuit in accordance with the present disclosure comprises a plurality of channels shaped, for example, like the channels (10) shown in FIG. 1. Each channel has a depth and a width. The fluid contained in the channels absorbs light. Depending on the circumstances (the particular species of algae used, the kind of solvent, etc.) each channel will have an optimum depth and width so that the most hydrogen or oil production is obtained. Such optimum depth will range from several microns to several centimeters.

On the other hand, the faster the reaction happens, the faster the liquid can flow through the meandering channel. Therefore, obtaining the desired result is a tradeoff between speed of the liquid, depth of the channels, and width of the channels. In particular, the more the mass of waste in the channel (i.e. the larger the channel) the longer the time it takes the algae to eat the waste. The person skilled in the art will understand that speed of reaction is a relevant factor, because the faster the oil can be digested, the greater the quantity of oil that will be made. This tradeoff can be solved both through microscale fluidic techniques and mesoscale fluidic techniques as defined herein.

Figure 6:
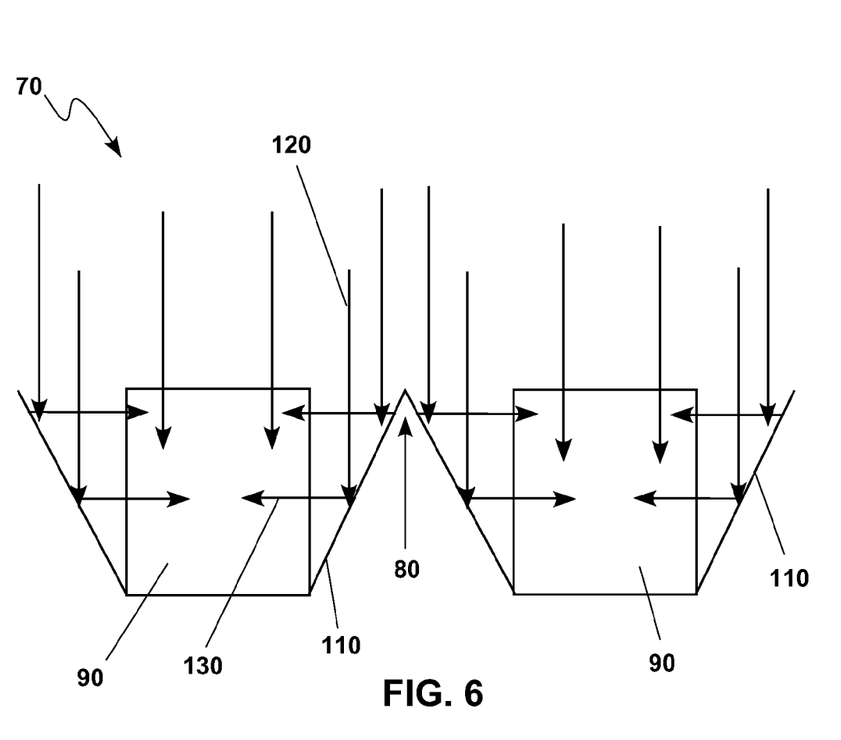
FIG. 6 shows an embodiment with mirrors.
Figure 7:
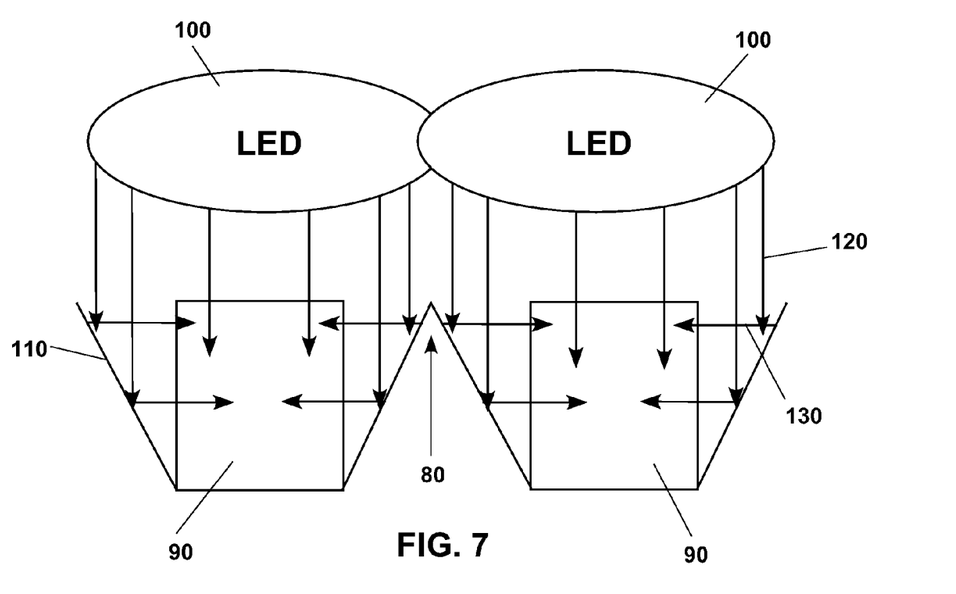
FIG. 7 shows an embodiment with mirrors and LEDs.

In accordance with these techniques, known as such to the person skilled in the art, a microscale or mesoscale circuit (or chip), to host the algae, will be provided. An interesting aspect of such circuit is the issue of sidewall light. In particular, the material of the chip acts as a lightguide. In this way, light that otherwise would be lost is sent to the algae. Such feature could be enhanced by design, if so wished. Reference can be made to FIGS. 6 and 7 of the present disclosure, later discussed in detail.

With reference to the algae, species of algae are so rich in oil that it accounts for over 15% of their mass are preferred. As selected by the National Renewable Energy Laboratory (NREL), approximately 300 species of algae satisfy to this requirement, such as diatoms (genera *Amphora, Cymbella, Nitzschia*, etc.) and green algae (genera *Chlorella* in particular). Samples of these algae are stored, for example, at the Marine Bioproducts Engineering Center (MarBEC).

In particular, all algae primary comprise the following compounds, in varying proportions: Proteins, Carbohydrates, Fats and Nucleic Acids. An exemplary indication of those proportions is shown in Table 1.

TABLE 1

Chemical Composition of Algae Expressed on A Dry Matter Basis (%)

| Strain | Protein | Carbohydrates | Lipids | Nucleic acid |
|---|---|---|---|---|
| Scenedesmus obliquus | 50-56 | 10-17 | 12-14 | 3-6 |
| Scenedesmus quadricauda | 47 | — | 1.9 | — |
| Scenedesmus dimorphus | 8-18 | 21-52 | 16-40 | — |
| Chlamydomonas rheinhardii | 48 | 17 | 21 | — |
| Chlorella vulgaris | 51-58 | 12-17 | 14-22 | 4-5 |
| Chlorella pyrenoidosa | 57 | 26 | 2 | — |
| Spirogyra sp. | 6-20 | 33-64 | 11-21 | — |
| Dunaliella bioculata | 49 | 4 | 8 | — |
| Dunaliella salina | 57 | 32 | 6 | — |
| Euglena gracilis | 39-61 | 14-18 | 14-20 | — |
| Prymnesium parvum | 28-45 | 25-33 | 22-38 | 1-2 |
| Tetraselmis maculate | 52 | 15 | 3 | — |
| Porphyridium cruentum | 28-39 | 40-57 | 9-14 | — |
| Spirulina platensis | 46-63 | 8-14 | 4--9 | 2-5 |
| Spirulina maxima | 60-71 | 13-16 | 6-7 | 3-4.5 |
| Synechoccus sp. | 63 | 15 | 11 | 5 |
| Anabaena cylindrical | 43-56 | 25-30 | 4-7 | — |

Source: Becker, (1994)

While the percentages vary with the type of algae, there are algae types that are comprised up to 40% of their overall mass by fatty acids. It is this fatty acid (oil) that can be extracted and converted into biodiesel by techniques identifiable by a skilled person. Algal-oil usually indicates very high in unsaturated fatty acids, such as Arachidonic acid (AA), Eicospentaenoic acid (EPA), Docasahexaenoic acid (DHA), Gamma-linolenic acid (GLA), Linoleic acid (LA), found in various algal-species.

Both fresh-water and salt-water algae, particularly rich in oils, can be selected. Molecular biology technology can be used to optimize the production of algae lipids, as well as their photosynthetic yield. As already mentioned above, other species of algae, capable of synthesizing hydrogen, are also the object of research.

In particular, green algae can produce hydrogen gas, $H_2$, in a process called "biophotolysis" or "photobiological hydrogen production." This process is carried out by photosynthetic enzymes, which split water to obtain electrons, excite these electrons with photons, and eventually use these electrons to reduce $2H+$ to $H_2$. It should be noted, however, that the enzyme that actually releases the hydrogen, the "reversible hydrogenase", is sensitive to oxygen. Given that the process of photosynthesis produces oxygen, hydrogen production is stopped very quickly in green algae. So, to overcome this problem, $O_2$-tolerant, $H_2$-producing mutants of the green alga *Chlamydomonas reinhardtii* are generated by various genetic approaches. In this way, a water-splitting process can be obtained that will result in a commercial $H_2$-producing system that is cost effective, scalable to large production, non-polluting, and self-sustaining.

Should gases need to be introduced or extracted from the device multilayer structures and/or membranes can be used. Also, in order to avoid oxygen poisoning, the channels can be made of oxygen impermeable material.

In particular, introduction of gas may be needed in order to make some algae work better by giving the algae the gas they need ($CO_2$) and taking away the gas they produce ($O_2$).

Figure 2:
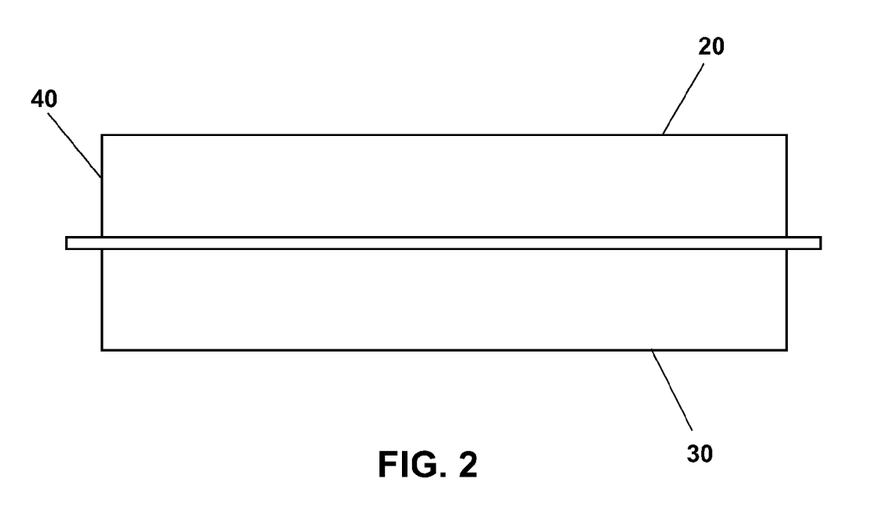
FIG. 2 shows an embodiment where additional channels for gas intake or collection are provided.

Reference can be made to FIG. 2, which shows a first channel (20), where the algae are located, and a second channel (30), where gas is introduced into or extracted from the arrangement of the present disclosure. Channels (20) and (30) are separated by a gas permeable membrane (40).

With reference to the waste, such waste can comprise anything the algae can live off of ranging from sewage to smokestack emissions, from liquid to solid to gas. The person skilled in the art will also understand that each algae is optimized to eat a different substance.

As already mentioned above, the meandering channel is also defined by parameters such as the width and the height of the channels. The present disclosure can also use meandering channels, i.e. meandering channels where one or more channels have at least one dimension (height or width) less then 10 cm. Microfluidics allows the surface area to be optimized and helps ensure that all the waste is converted, helping to optimize both the "efficiency" and "time efficiency" of algae fuel production by creating a large surface area, so that both are enhanced. Microfluidic channels can be in the 1 to 1000 micrometer range. Mesofluidic channels can be in the 1 to 200 mm range.

In accordance with the present disclosure, combined with the desired width-to-height ratio of the microfluidic or mesofluidic meandering channel, a mix of algae and animal or human waste can be flowed into the channel, and the algae can be allowed to feed on the waste in the presence of sunlight. A desired width-to-height ratio is a ratio where optimum production is reached. For example, the optimal size of the meandering channels could be much larger than microfluidic circuits, as large as inches or even feet. "Optimum production" is here intended to mean the fastest time to do the most oil or hydrogen.

In particular, control over the following variables can be exerted: width, height, flow, light collection, sidewall light penetration, and gas input/output. Both flow and gas can be mixed. For example, with reference to flow, this can done by i) pulsing, ii) pushing back and forth, iii) surface features, or any traditional microfluidic or mesofluidic mixing method.

Making sure that the algae are well mixed with the waste is an important feature of the present disclosure. Reference can be made to A. D. Stroock, S. K. Dertinger, A. Ajdari, I. Mezic, H. A. Stone, G. M. Whitesides "Chaotic Mixer for Microchannels", Science 25 Jan. 2002, Vol. 295 no. 5555, pp. 647-651, incorporated herein by reference in its entirety, where the issue of mixing solutions in microchannels is addressed. In particular, under typical operating conditions, flows in these channels are laminar—the spontaneous fluctuations of velocity that tend to homogenize fluids in turbulent flows are absent, and molecular diffusion across the channels is slow. In the above paper a passive method is presented for mixing streams of steady pressure-driven flows in microchannels at low Reynolds number. Using this method, the length of the channel required for mixing grows only logarithmically with the Péclet number, and hydrodynamic dispersion along the channel is reduced relative to that in a simple, smooth channel. This known method uses bas-relief structures on the floor of the channel that are easily fabricated with commonly used methods of planar lithography.

Therefore, mixing can be achieved by the use of microfluidics. Alternatively, mixing can be achieved by pushing and pulling back and forth, or going around a circle, or just by diffusion in the long channels of the meandering circuit. With reference to gases, they can mix themselves if injected correctly. With reference to later discussed FIG. 5, the presence of pores (50) allows for a correct injection of these gases.

The meandering channel can be made of a transparent material such as polydimethylsiloxane (PDMS). The channels can be defined photolithographically with a rapid prototyping system, or with a mold made of some other material (like plastic or metal).

The algae will eat the waste and convert it to a usable form that can be collected by flowing a solvent through the channel in order to push it out. In particular, once the algae turn into oil after having eaten the waste, they have to be collected. This can happen by having, for example, a continuous flow at a particular rate, so that oily algae are collected at the end of the process. Alternatively, a batch process can be provided, where collection begins once all of the algae have turned into oil, and then oil is pushed out with the solvent. Therefore, either a continuous collection process or a batch collection process can be provided. Collection will allow hydrogen or oil to be collected.

The channels can be arranged in a parallel-serial fashion in order to aid the extraction of the algae for use in making biodiesel. In this way, the path length that the algae have to be subjected to in order to be pushed along the meandering channel is decreased. It follows that less pressure can be used when trying to extract the algae with solvent or other liquid.

Figure 3:
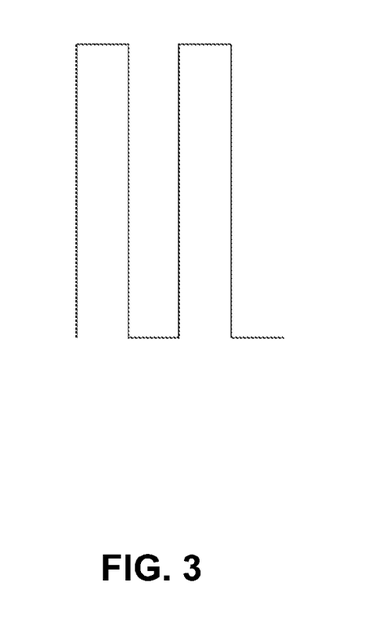
FIG. 3 shows a serial path of a meandering channel.
Figure 4:
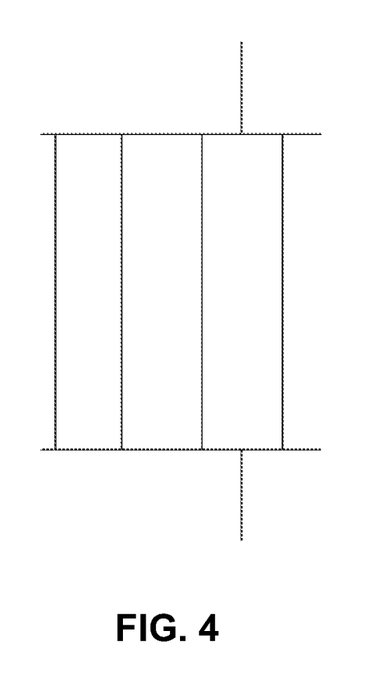
FIG. 4 shows a parallel path of a meandering channel.

FIG. 3 shows a serial path of a meandering fluid channel, while FIG. 4 shows a parallel path for the meandering fluid channel. The path length of FIG. 3 is four legs, while the path length for FIG. 4 is also four legs. Both the series embodiment and the parallel embodiment require the same length of channel, so they both hold the same amount of algae. The parallel embodiment can be useful for batch processing, while the serial embodiment is better for serial processing.

Figure 5:
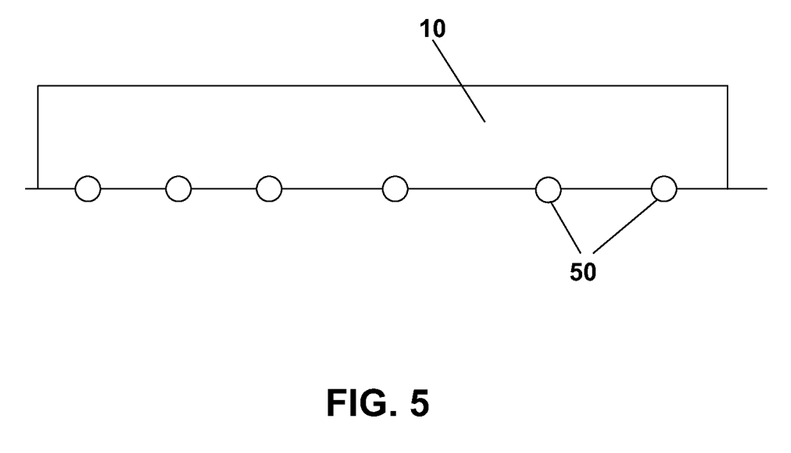
FIG. 5 shows a meandering channel comprising pores.

Additionally, smaller channels or pores on the walls of the channel can have solvent flowed through them. According to an embodiment of the present disclosure, the pores will cover the entire (or a large part) of the surface area of the channel and will facilitate the quick dissolving of the algae into the solution and out to the collection point. FIG. 5 shows a cross section of a channel (10), comprising a plurality of pores (50) at its bottom.

Channels can either be closed or open on top. Fluid control can be better obtained with closed channels. However, open channels are useful for drying operations. According to an embodiment of the present disclosure, channels can have a top cover than can be open or closed according to the circumstances. In this embodiment, channels can be filled when their top cover is closed and then the top cover can be taken away so that they will dry very quickly. This embodiment can be useful for collection and drying.

In this way, large or small "solar panels" of biodiesel making algae, or any other form of useful algae, can be exposed to the sun with maximum surface area usage efficiency and also solvent efficiency. A possible surface area of the solar panels obtained through the present disclosure can range from 1 $m^2$ to 5 $m^2$. Additionally, other forms of chemical or biological reactions can be performed and occur.

According to a further embodiment, the solar panels can be exposed to artificial light at night, such as light produced by a LED (light-emitting-device). Moreover, waveguides can be fashioned into the panel to spread the light evenly and efficiently. Further, a light source can be used. The LED's are useful, because they can be specifically tuned to the optimal wavelength of the algae production, thus saving energy.

For example, FIG. 6 shows an embodiment where light (70) coming from the top is reflected through triangle mirrors (80) into the channels (90). The channels and the mirrors are so constructed to mate with each other. FIG. 7 shows a further embodiment where LEDs (100) are also provided, to further provide light in absence of natural light, e.g., at night. The embodiments of FIGS. 6 and 7 also illustrate the previously mentioned concept of "sidewall light." In particular, walls (110) of the mirror allow light through rays (120) (i.e. those rays that do not go directly to the channels) to be reflected and also reach the channel through rays (130).

In a further embodiment, the algae are in a liquid with index of refraction N1, the device or chip is made with index of refraction N2, and the channel design is such that a large amount of light incident on N2 is guided into N1 where the algae are. This embodiment can be performed with a sawtooth design of the channel walls or just by carefully selecting N1 vs. N2. Moreover, the top of the chip can be lens shaped to concentrate the light that would go into the non-channel region of the chip into the algae. This feature can be obtained with replication molding (a mold with the lens shape can be made and molded into the chip).

Figure 8:
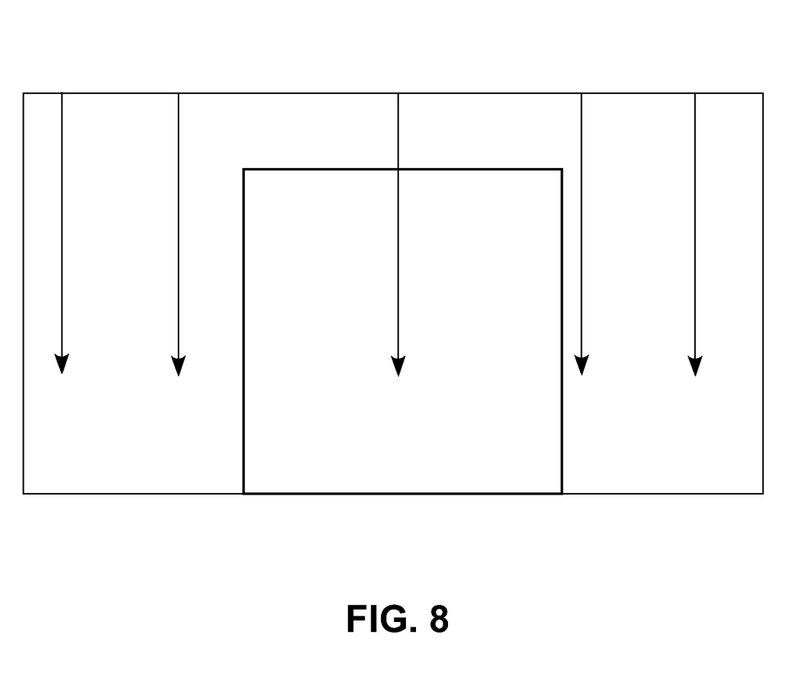
FIGS. 8 and 9 show the top surface of the device of the present disclosure.
Figure 9:
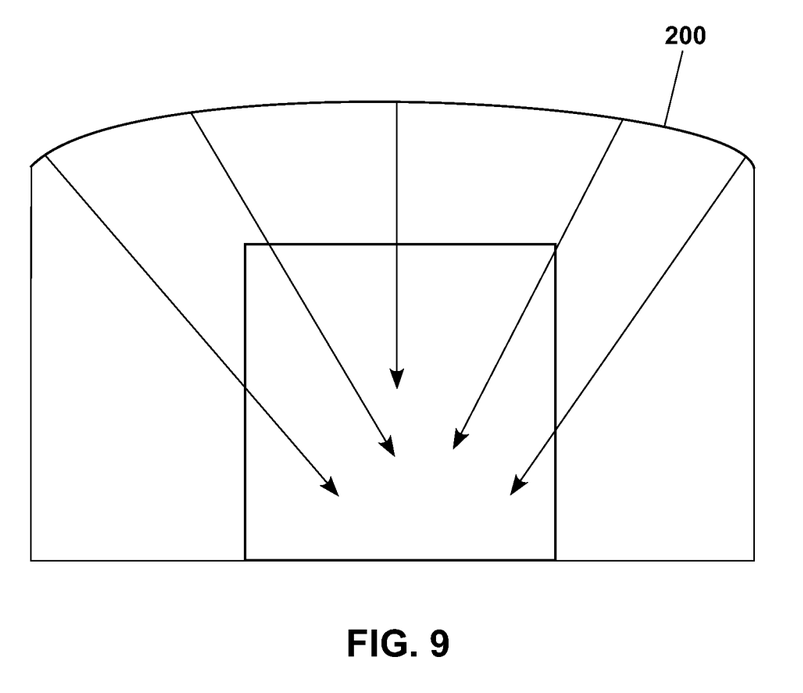

FIGS. 8 and 9 shows schematic views in accordance with what discussed in the previous paragraph. In particular, FIG. 8 shows an embodiment where the top surface (200) of the device in accordance with the present disclosure does not have a lens shape. This embodiment is suited for applications where the presence or amount of sidewall light is not desired. On the other hand, the embodiment of FIG. 9 shows a top surface (210) having a lens shape, in particular a convex lens shape. In the embodiment of FIG. 9 a higher amount of light is channeled towards the algae. In particular, the lens shape maximizes the light that falls in the channels containing the algae or concentrates the light in those channels.

With reference to the light source, the wavelength of the light source can be chosen such that minimum power is used. In particular, it is known that algae produce more oil at certain wavelengths. See, for example, T. You, S. M. Barnett "Effect of Light Quality on Production of Extracellular Polysaccharides and Growth Rate of *Porphyridium Cruentum*", Biochem. Eng. J. 2004, vol. 19, no. 3, pp. 251-258. See also C. Sorokin, R. W. Krauss "The Effects of Light Intensity on the Growth Rates of Green Algae", Plant Physiol. 33: 109-113 (1958). Both of these papers are herein incorporated by reference in their entirety.

Therefore, there is no need to spend powers at wavelengths not of interest for the particular reaction at issue. As a consequence, the wavelength of maximum algae activity can be used to increase efficiency.

The specific embodiments set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the described devices systems and methods that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

It is to be understood that the inventions are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

What is claimed is:

1. A method of reacting biological or chemical material comprising:
    providing a chamber shaped as a meandering fluid channel, wherein each channel of the meandering fluid channel has a channel height, a channel width, a channel to region and channel sidewalls formed by two sidewalls of the meandering fluid channel;
    placing the biological or chemical material in the chamber;
    subjecting, via the channel to regions and the channel sidewalls, the biological or chemical material to light for a time and under conditions to allow the biological or chemical material to react;
    obtaining an optimum production, defined as the fastest time to produce the highest amount of a reaction product;
    based on the obtaining, pushing the reaction product out of the chamber; and
    based on the pushing, collecting the reaction product,
    wherein the channel height and the channel width are derived using the steps of:
        (i) defining a first optimum point of production as the fastest time to obtain the reaction product and a second optimum point of production as the highest amount of the reaction product; and
        (ii) selecting a value of the channel height to channel width ratio taking into account both the first optimum point and the second optimum point.

2. The method of claim 1, wherein the biological or chemical material is placed in the chamber together with a further reactant.

3. The method of claim 2, wherein the biological or chemical material is algae, the further reactant is biomass or growth medium, and the reaction is algae growth.

4. The method of claim 3, wherein the algae are algae containing oil accounting for at least 15% of the algae's mass.

5. The method of claim 4, wherein the algae are diatoms or green algae.

6. The method of claim 4, wherein the algae are fresh-water or salt-water algae.

7. The method of claim 3, wherein the algae are hydrogen-generating algae.

8. The method of claim 3, wherein the algae are hydrogen-generating mutant algae.

9. The method of claim 3, wherein the channel height to width ratio is chosen to optimize volume of oil or hydrogen obtained from the algae with respect to volume of the biomass.

10. The method of claim 3, wherein the channel height to width ratio is chosen to optimize volume of oil or hydrogen obtained from the algae with respect to time.

11. The method of claim 3, wherein the biomass comprises human or animal waste.

12. The method of claim 2, wherein said second optimum point corresponds to a mass or volume of a product of the reaction per mass or volume of said further reactant.

13. The method of claim 1, wherein the chamber is a microfluidic chamber.

14. The method of claim 1, wherein the chamber is a mesofluidic chamber.

15. The method of claim 1, wherein the channel top regions face towards the light and the channels are open on each said channel top region.

16. The method of claim 1, wherein the channels are closed on top.

17. The method of claim 1, wherein the channel top regions face towards the light and opening or closing of the channels on each said channel top region is controllable.

18. The method of claim 1, wherein the light is solar light.

19. The method of claim 1, wherein the light is artificial light.

20. The method of claim 19, wherein the artificial light comprises at least one LED.

21. The method of claim 1, wherein the channel sidewalls of the meandering fluid channel comprise pores.

22. The method of claim 21, wherein gas or solvent is flown into and/or out the meandering fluid channel through the pores.

23. The method of claim 1, wherein the pushing further comprises creating a continuous flow of the reaction product at a particular rate so that the reaction product is collected continuously.

24. The method of claim 23, wherein the reaction product is suitable for producing biodiesel.

25. The method of claim 1, wherein the pushing further comprises waiting for the entirety of the biological or chemical material to react, and based on the waiting, pushing the reaction product out of the chamber in batch.

26. The method of claim 1, further comprising providing one or more mirrors, associated with the channels, to reflect light from a light source onto the channel sidewalls.

27. The method of claim 26, wherein the one or more mirrors are sawtooth mirrors.

28. The method of claim 26, wherein the one or more mirrors are placed in a gap created by a separation of the channel sidewalls.

29. The method of claim 1, wherein said first optimum point corresponds to a mass or volume of a product of the reaction divided by time unit.

30. The method of claim 1, wherein the channel has an optimum depth, the optimum depth ranging from microns to centimeters.

31. The method of claim 1, wherein at least one of the channel height and channel width is less than 10 cm.

32. The method of claim 1, wherein a material of the channel sidewalls is selected for operation of the channels sidewalls as light guides, such as to allow efficient usage of the light.

33. The method of claim 1, wherein the channel sidewalls have a sawtooth design such as to increase an amount of light during the subjecting of the biological or chemical material to light.

* * * * *